United States Patent
Alvarez et al.

(10) Patent No.: US 6,370,413 B1
(45) Date of Patent: Apr. 9, 2002

(54) ULTRASOUND IMAGING SYSTEM AND METHOD TO ARCHIVE AND REVIEW 3-D ULTRASOUND DATA

(75) Inventors: Raul Alvarez, Fall City; Christian Deforge, Seattle; David Edward Nielsen, Issaquah, all of WA (US)

(73) Assignee: Siemens Medical Solutions USA, Inc., Iselin, NJ (US)

( * ) Notice: Subject to any disclaimer, the term of this patent is extended or adjusted under 35 U.S.C. 154(b) by 0 days.

(21) Appl. No.: 09/433,616

(22) Filed: Nov. 2, 1999

(51) Int. Cl.7 .............................. A61B 5/00; A61B 8/00; G06T 15/00
(52) U.S. Cl. ...................... 600/407; 600/437; 128/916; 345/424
(58) Field of Search ................................. 600/407, 437, 600/443, 447, 916; 711/100; 369/13; 345/419–422, 424, 425, 530, 531, 553, 565

(56) References Cited

U.S. PATENT DOCUMENTS

| | | | |
|---|---|---|---|
| 5,628,320 A | 5/1997 | Teo | 128/660.07 |
| 5,797,845 A | 8/1998 | Barabash et al. | 600/443 |
| 5,876,342 A | 3/1999 | Chen et al. | 600/443 |
| 5,928,151 A | 9/1999 | Hossack et al. | 600/443 |
| 5,986,662 A | * 11/1999 | Argiro et al. | 345/424 |
| 6,005,592 A | * 12/1999 | Koizumi et al. | 345/517 |
| 6,083,162 A | * 7/2000 | Vining | 345/424 |
| 6,144,384 A | * 11/2000 | Nakazawa | 345/424 |

* cited by examiner

Primary Examiner—Francis J. Jaworski

(57) ABSTRACT

A system and a method of managing 2-D images, as well as any saved 3-D volume data that was used to derive the 2-D images, utilize a bookmark saver that operates to automatically save, for each 2-D image saved, the settings of viewing parameters for the corresponding 3-D volume data when the 2-D image was saved. The automatic saving feature executed by the bookmark saver ensures that the underlying 3-D volume data, if saved, is retrieved in the viewing configuration that was set when the 2-D image of interest was saved. This feature allows a user of the system to efficiently return to work that was previously suspended or terminated. In an exemplary embodiment, the system is an ultrasound imaging system. However, the system may also be an imaging system based on magnetic resonance, computed tomography technology, or other modalities. In a preferred embodiment, the 2-D bitmap data of the 2-D image being saved and the viewing parameters that were used to manipulate the underlying 3-D volume data are saved in the same data file, known as a "bookmark." The bookmark also includes information that identifies the corresponding 3-D volume, which allows the system to infer the existence of a relationship between the 2-D image and the underlying 3-D volume by searching to see if the underlying 3-D volume had been saved, thereby eliminating the need to store such information in a database.

18 Claims, 4 Drawing Sheets

ULTRASOUND IMAGING SYSTEM AND METHOD TO ARCHIVE AND REVIEW 3-D ULTRASOUND DATA

BACKGROUND OF THE INVENTION

The invention relates generally to ultrasound imaging systems and more particularly to an ultrasound imaging system that can acquire three-dimensional volume data of anatomical structures.

DESCRIPTION OF THE RELATED ART

Ultrasound imaging systems are widely used for medical diagnostic applications. In more complex systems, three-dimensional (3-D) volume data of anatomical structures can be ultrasonically acquired, as well as the typical two-dimensional (2-D) images. In such systems, the acquired 3-D volume data can be used to view virtual anatomical structures in different configurations by manipulating the 3-D volume data to display 2-D images. As an example, the 3-D volume data can be viewed by slicing through the displayed volume data at some arbitrary user-specified location or by using one of the available volume rendering algorithms.

A "3-D ultrasound volume" is defined herein as a construction of ultrasound information relating to three dimensions of a target. As one example, a 3-D ultrasound volume may be formed by assembling a number of ultrasonically acquired frames (or slices) of pixel data, with each frame representing a cross section along a different plane through the target volume. Combining the frames of pixel data is one approach to providing a 3-D ultrasound volume of 3-D volume data.

During an ultrasound examination using a conventional 3-D ultrasound imaging system, one or more 3-D ultrasound volumes (of B, power, color, etc. information) from an anatomical structure of a patient may be acquired by a sonographer. Each acquired 3-D volume can then be manipulated in different configurations to render multiple 2-D images from the 3-D volume data. These 2-D images are saved for subsequent review by a physician for evaluation or diagnosis. Each viewing configuration of the 3-D volume data requires the input of a set of viewing parameters to define the desired rendering. In general, the 2-D images are captured and saved in a sequential manner during operations in which the 3-D volume data is manipulated to render a different viewing configuration for each subsequent 2-D image. The underlying 3-D volume data for the saved 2-D images may also be saved for subsequent retrieval.

If a particular 3-D volume is saved, the sonographer can capture additional 2-D images from that 3-D volume at a later time. However, the sonographer will have to re-enter the viewing parameters to manipulate the 3-D volume data to a desired viewing configuration, which would typically be the viewing configuration that was defined when the last 2-D image was captured and saved. It can take the sonographer some time to set the right parameters for the desired viewing configuration. It may also be impossible for the sonographer to set the viewing configuration from the previously saved 2-D image. Thus, capturing additional 2-D images from saved 3-D volume data can be a tedious task. Due to this inconvenience, a sonographer is motivated to use the examination time to capture and save all of the 2-D images that may be of interest at a later time. Of course, this prolongs the duration of the examination.

In light of the above concern, what is needed is an ultrasound imaging system and a method of managing the saved 2-D images and their underlying 3-D volume, such that it is more convenient and efficient to acquire additional 2-D images from the 3-D volume data after the initial ultrasound examination.

SUMMARY OF THE INVENTION

A system and a method of managing 2-D images, as well as any saved 3-D volume data that was used to derive the 2-D images, utilize a bookmark saver that operates to automatically save, for each 2-D image saved, the settings of viewing parameters for the corresponding 3-D volume data when the 2-D image was saved. The automatic saving feature executed by the bookmark saver ensures that the underlying 3-D volume data, if saved, is retrieved in the viewing configuration that was set when the 2-D image of interest was saved. This feature allows a user of the system to efficiently return to work that was previously suspended or terminated. The system may be an imaging system based on ultrasound, magnetic resonance, computed tomography technology, or other modalities. Alternatively, the system may be a conventional computer system that embodies the bookmark saver.

In an exemplary embodiment, the system includes an ultrasonic scanhead, a processing unit, an input device, and a display device. The scanhead includes an array of piezoelectric elements to transmit sound waves and to receive echoes of the transmitted ultrasound waves that are reflected from an anatomical structure of interest. The scanhead operates to convert the received echoes into electrical signals. The scanhead is electrically coupled to the processing unit, which processes the electrical signals to generate 3-D ultrasound volume data that electronically represents the anatomical structure of interest. The input device functions as a user interface and may include a standard computer keyboard and a pointing device. The display device may be a CRT or an LCD monitor.

The processing unit of the system includes a scanhead controller, memory, the bookmark saver, a removable storage device, a network interface, and a processor. The scanhead controller is operatively connected to the ultrasonic scanhead to control the transmitting and receiving operations of the scanhead. The removable storage device may utilize one of a number of removable storage media that are currently available, such as a writeable CD, a DVD, or a magneto-optical storage medium. Alternatively, the removable storage device may be an on-system storage device, i.e., a hard disk drive.

The bookmark saver of the processing unit is configured to operate with the processor to automatically save the settings of viewing parameters for the underlying 3-D ultrasound volume data whenever a 2-D image is saved. The bookmark saver may be implemented in the processing unit as hardware and/or software. In a preferred embodiment, the bookmark saver operates to embed the information regarding the viewing parameters into a data file called a "bookmark." The bookmark contains the 2-D bitmap data of the saved 2-D image and the information identifying which 3-D ultrasound volume data corresponds to the 2-D image, as well as the viewing parameter information. Since the viewing parameter information and the identifying information are embedded with the 2-D image data, there is no need to store such information in a database.

By storing 2-D images as well as bookmarks, older PACS systems are not precluded from using images generated by the ultrasound imaging system. When the system interacts with PACS, the system can decide to send either 2-D images or 2-D images, bookmarks and volumes, depending on the PACS's capabilities. The advantage to the physician is that he/she does not have to choose between a bookmark and an image.

The method in accordance with the present invention includes a step in which 3-D ultrasound volume of an anatomical structure of a patient is acquired using known ultrasound 3-D imaging techniques. Next, the acquired 3-D ultrasound volume is manipulated to a viewing configuration using a number of viewing parameters to capture a 2-D image from the 3-D ultrasound volume data. As an example, the viewing parameters may include orientation, geometry, rendering algorithm (e.g., surface rendering and arbitrary slicing), colormaps, and ultrasound imaging parameters. The exact types of viewing parameters that are used to manipulate the 3-D ultrasound volume data are not critical to the invention.

After the 3-D ultrasound volume data has been manipulated to the desired viewing configuration, the 2-D image is saved in accordance with the instructions of the user of the ultrasound imaging system. The 2-D image may be saved in the memory or in the removable storage device of the system or network. In response to the saving of the 2-D image, the bookmark saver of the processing unit automatically saves the viewing parameters. Furthermore, the bookmark saver saves the information that identifies the 3-D ultrasound volume from which the 2-D image was derived. In a preferred embodiment, the 2-D bitmap data of the 2-D image, the viewing parameter settings, and the identification information are collectively saved as a bookmark file. Additional 2-D images may be derived from the acquired 3-D ultrasound volume by changing one or more viewing parameters to manipulate the 3-D ultrasound volume data to a different viewing configuration. Furthermore, additional 3-D ultrasound volumes of the same or a different anatomical structure of the patient may be acquired by repeating the above-described steps. If repeated, one or more 2-D images may be derived from each additionally acquired 3-D ultrasound volume.

Each 3-D ultrasound volume may be saved anytime after that 3-D ultrasound volume is acquired. After all the 3-D ultrasound volumes of interest and the viewing parameters for each desired 2-D image have been saved, one or more of the saved 2-D images can be reviewed by displaying the 2-D images on the display device of the system. Assuming that the underlying 3-D ultrasound volume for a particular 2-D image had been previously saved, the 3-D ultrasound volume can then be retrieved using the saved viewing parameters, such that the 3-D volume is in the same viewing configuration as when the 2-D image was saved.

An advantage of the preferred embodiment of the invention is that since the bookmark contains information that identifies which 3-D ultrasound volume is the underlying data for the 2-D image stored in the bookmark, data regarding the existence of a relationship between the 2-D image and the underlying 3-D volume need not be stored. Instead, the relationship can be inferred by simply searching the system to see if the underlying 3-D ultrasound volume had been saved.

Another advantage is that the retrieved 3-D ultrasound volume is in the same viewing configuration as when a particular 2-D image was saved, which eliminates the need to reset the viewing parameters to manipulate the retrieved 3-D ultrasound volume data to that viewing configuration.

DETAILED DESCRIPTION

Figure 1:
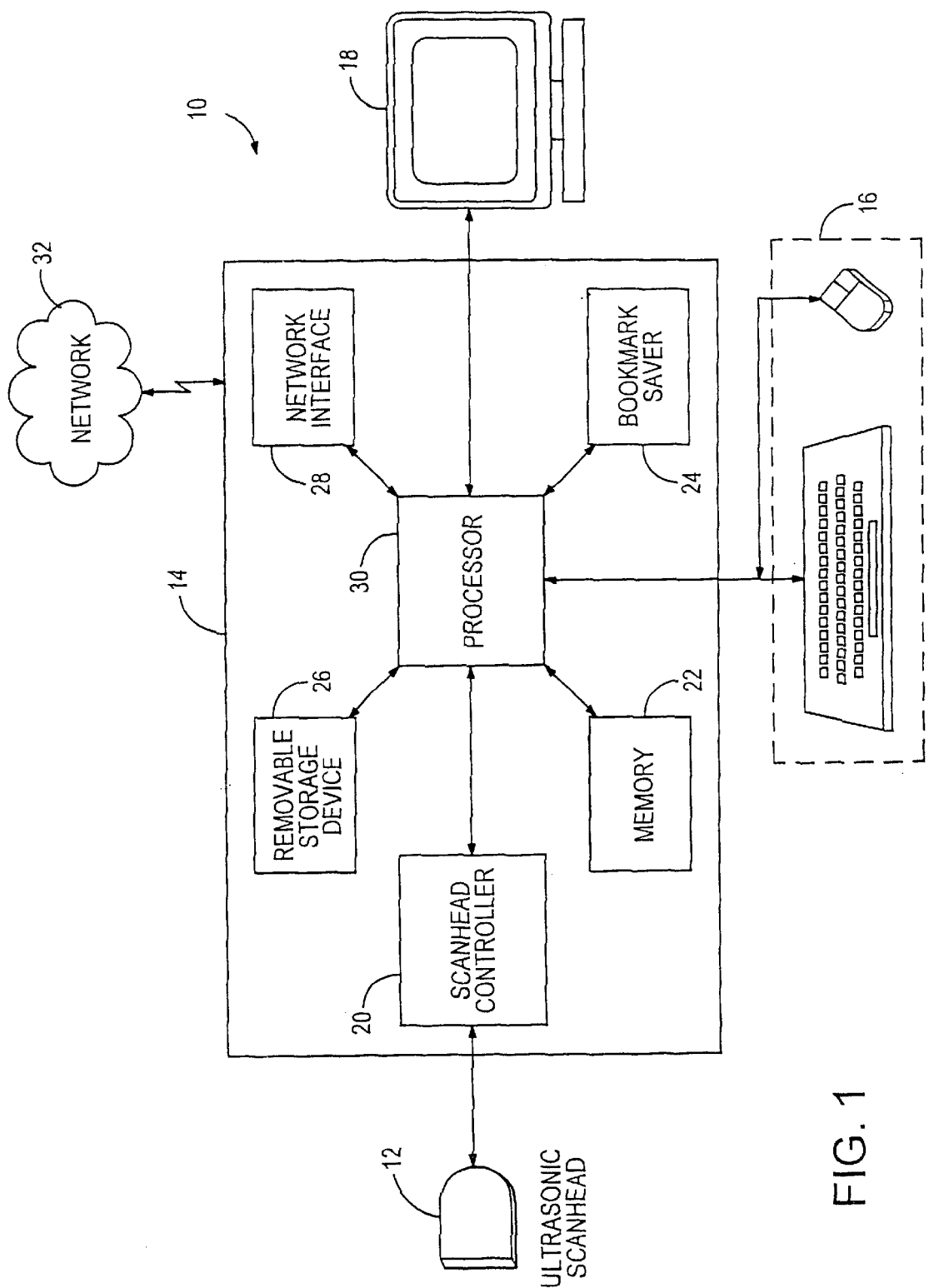
FIG. 1 is a schematic diagram of an ultrasound imaging system in accordance with an exemplary embodiment of the present invention.

With reference to FIG. 1, an ultrasound imaging system 10 in accordance with an exemplary embodiment of the present invention is shown. The system is designed to acquire one or more 3-D ultrasound volumes during an ultrasound examination by transmitting ultrasound waves and receiving echoes of the transmitted ultrasound waves that are reflected from the anatomical structure being examined. An acquired 3-D ultrasound volume may be manipulated to capture and save 2-D images from the 3-D ultrasound volume. The system operates to save viewing parameters that were used to manipulate the underlying 3-D ultrasound volume to a specific configuration when a particular 2-D image is saved, as well as the information that identifies which 3-D ultrasound volume is the underlying data for that 2-D image. The saved viewing parameters allow a user to retrieve the underlying 3-D ultrasound volume data, if saved, in the specific configuration into which the 3-D ultrasound volume was manipulated when the 2-D image of interest was captured and saved. Thus, the user of the ultrasound imaging system does not have to re-enter the viewing parameters to manipulate the 3-D volume data into the previously set configuration.

The ultrasound imaging system 10 includes an ultrasonic scan-head 12, a processing unit 14, an input device 16, and a display device 18. The ultrasonic scanhead includes an array of piezoelectric elements that generates ultrasound waves in response to electrical signals of proper voltage and frequency. As is well known in the art, the piezoelectric element array of the scanhead also generates electrical signals in response to mechanical vibrations caused by return echoes of the ultrasound waves. These return echoes are processed by the processing unit to three-dimensionally image an anatomical structure of interest.

The input device 16 of the system 10 may include a standard computer keyboard and a pointing device, as shown in FIG. 1. The input device is used as a user interface to control the functions of the system, such as initiating ultrasound imaging, acquiring 3-D ultrasound volume data for a particular anatomical structure, manipulating the acquired 3-D ultrasound volume data, capturing and saving 2-D images from the manipulated 3-D ultrasound volume data, and retrieving an underlying 3-D ultrasound volume from a designated 2-D image. The display device 18 of the system may be a conventional computer monitor, such as a CRT or an LCD monitor.

The processing unit 14 is designed to perform various signal processing procedures that are required for proper operation of the ultrasound imaging system. Included in the processing unit are a scanhead controller 20, memory 22, a bookmark saver 24, a removable storage device 26, a network interface 28, and a processor 30. The scanhead controller is operatively connected to the ultrasonic scan-head 12 to control the transmitting and receiving operations of the scanhead. The memory may be a standard hard disk drive that is commonly found in a typical personal computer.

The removable storage device may utilize one of a number of removable storage media that are currently available, such as a writeable CD, a DVD, or a magneto-optical storage medium. Alternatively, the removable storage device may be an on-system storage device, such as a hard disk drive. The network interface may include a modem or an ethernet card that allows the system to be connected to a network 32. The network may be any type of network, such as a LAN, a WAN, or the Internet.

The bookmark saver 24 of the processing unit 14 is configured to operate with the processor 30 to automatically save the current settings of the viewing parameters that were used to manipulate the underlying 3-D ultrasound volume data to a specific viewing configuration to capture a 2-D image from the 3-D volume. The automatic saving of the viewing parameters occurs whenever a 2-D image is saved. After a 3-D ultrasound volume of an anatomical structure has been acquired by the ultrasound imaging system 10, the 3-D ultrasound volume can be manipulated into a desired viewing configuration by setting the viewing parameters. These viewing parameters may include orientation, geometry, rendering algorithm (e.g., surface rendering and arbitrary slicing), colormaps, ultrasound imaging parameters, and other common parameters that are used to view 3-D ultrasound volumes. The exact types of viewing parameters used are not critical to the invention. The viewing parameters can be set by entering instructions into the system using the input device 16. The saved viewing parameters allow a user to retrieve a particular 3-D volume in the configuration that was set when a 2-D image of interest was saved. Thus, the configuration of the retrieved 3-D ultrasound volume data will depend on the 2-D image that is being used to retrieve the 3-D volume. This feature increases work-flow flexibility by allowing the user to return to work that was previously suspended or terminated without the need to reset the viewing parameters to manipulate the 3-D volume to the last configuration. The bookmark saver may be implemented in software and/or hardware. The specific implementation of the bookmark saver is not critical to the invention.

Figure 2:
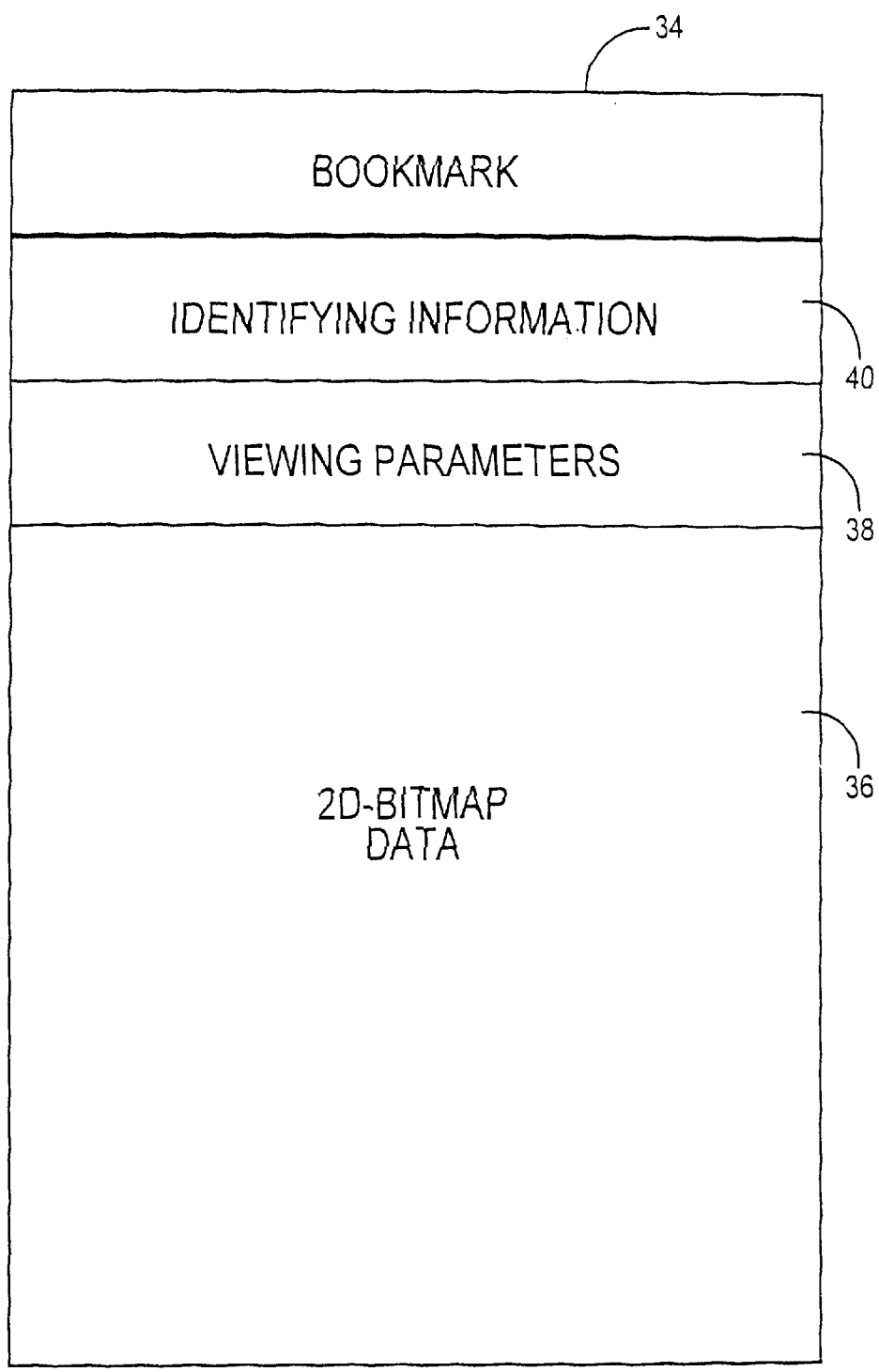
FIG. 2 is a block diagram of a bookmark, which illustrates the types of data contained within the bookmark.

In a preferred embodiment, the viewing parameters are saved by the bookmark saver 24 in a bookmark. A "bookmark" is defined herein as a data file that contains the 2-D bitmap data of the 2-D image being saved, the viewing parameters that were used to manipulate the underlying 3-D ultrasound volume data when the 2-D image was saved, and information that identifies the 3-D volume from which the saved 2-D image was derived. An exemplary bookmark 34 is schematically illustrated in FIG. 2. The bookmark is shown to include 2-D bitmap data 36, viewing parameters 38 and identifying information 40. Since the viewing parameters are saved in the same file as the 2-D bitmap data, the system only needs to read the bookmark to display the 2-D image and to retrieve the underlying 3-D ultrasound volume, if previously saved, in the configuration to which the 3-D volume data had been manipulated when the 2-D image was saved. Thus, the viewing parameters need not be saved in a database.

The ultrasound imaging system 10 is configured such that the bookmark saving procedure is independent of the saving procedure for the underlying 3-D ultrasound volume. That is, saving the bookmark does not depend on whether the underlying 3-D ultrasound volume has been saved. Since 3-D ultrasound volume is quite large and takes a substantial amount of time to save, the system allows the user to independently decide whether or not to save the 3-D volume. Thus, the 3-D ultrasound volume may be saved before or after the bookmark has been saved, and may not even be saved. Regardless of whether the 3-D ultrasound volume has been saved, the bookmark contains the information that identifies the 3-D volume from which the 2-D image data of the bookmark was derived. This implies that a relationship between the 3-D volume and the bookmark may or may not exist. Unlike conventional ultrasound imaging systems in which the relationship information is stored in a database, the relationship information is not stored by the system 10. Instead, the relationship information is inferred at runtime by reading the identifying information from the bookmark and determining whether the underlying 3-D ultrasound volume is saved.

After one or more 2-D images have been saved for each acquired 3-D ultrasound volume, the saved 2-D images can be displayed on the display device 18 of the ultrasound imaging system 10. The saved 2-D images may be displayed individually or may be collectively displayed on the display device. The exact manner in which the saved 2-D images are displayed on the display device is not critical to the invention.

By storing 2-D images as well as bookmarks, older PACS systems are not precluded from using images generated by the ultrasound imaging system 10. When the system interacts with PACS, the system can decide to send either 2-D images or 2-D images, bookmarks and volumes, depending on the PACS's capabilities. The advantage to the physician is that he/she does not have to choose between a bookmark and an image.

Figure 3:
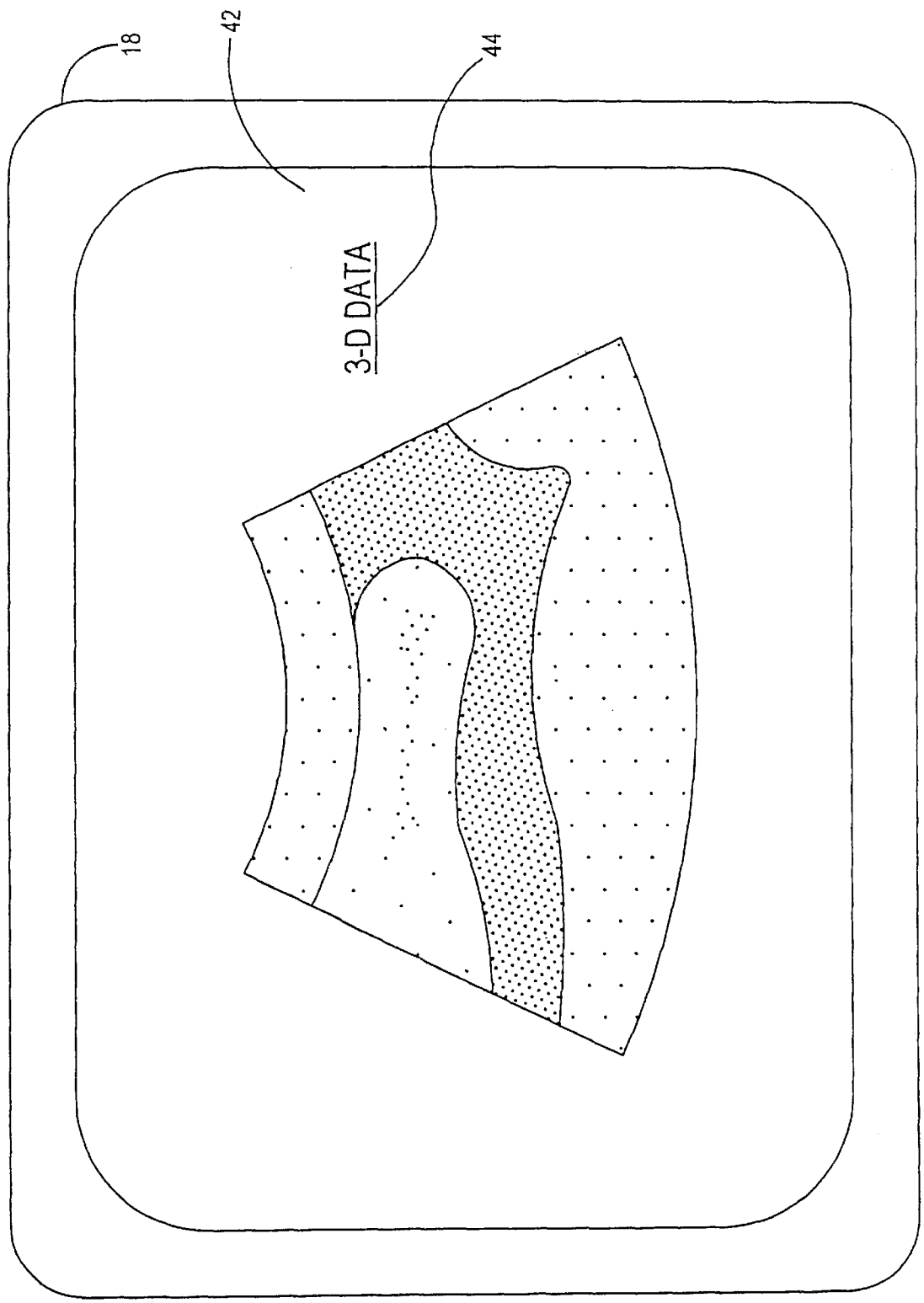
FIG. 3 is an exemplary screen shot of a 2-D image that is displayed on the display device of the system of FIG. 1 for review.

Turning to FIG. 3, an exemplary screen shot of an individually displayed 2-D image 42 is shown. The 2-D image includes a visual cue 44 that indicates whether the underlying 3-D ultrasound volume data has been saved. As shown in FIG. 3, the visual cue may, for example, be in a form of a string text that can either be highlighted or dimly displayed. A highlighted text may indicate that the underlying 3-D ultrasound volume has been saved and, consequently, can be recalled. On the other hand, a dimly displayed text may indicate that the underlying 3-D ultrasound volume has not been saved and cannot be recalled. The text may be a hyperlink, i.e., an underlined text string that is commonly found in web sites on the Internet. Thus, the underlying 3-D ultrasound volume may be recalled by clicking on the text using the pointing device of the input device 16, if the 3-D ultrasound volume had been saved. When recalled, the 3-D ultrasound volume is displayed on the display device 18 in the same configuration as when the 2-D image was saved by using the viewing parameters that were saved in the bookmark along with the 2-D image data. In an alternative embodiment, the visual cue 44 can be a pictorial graphic element, such as a bitmap image of an object.

Figure 4:
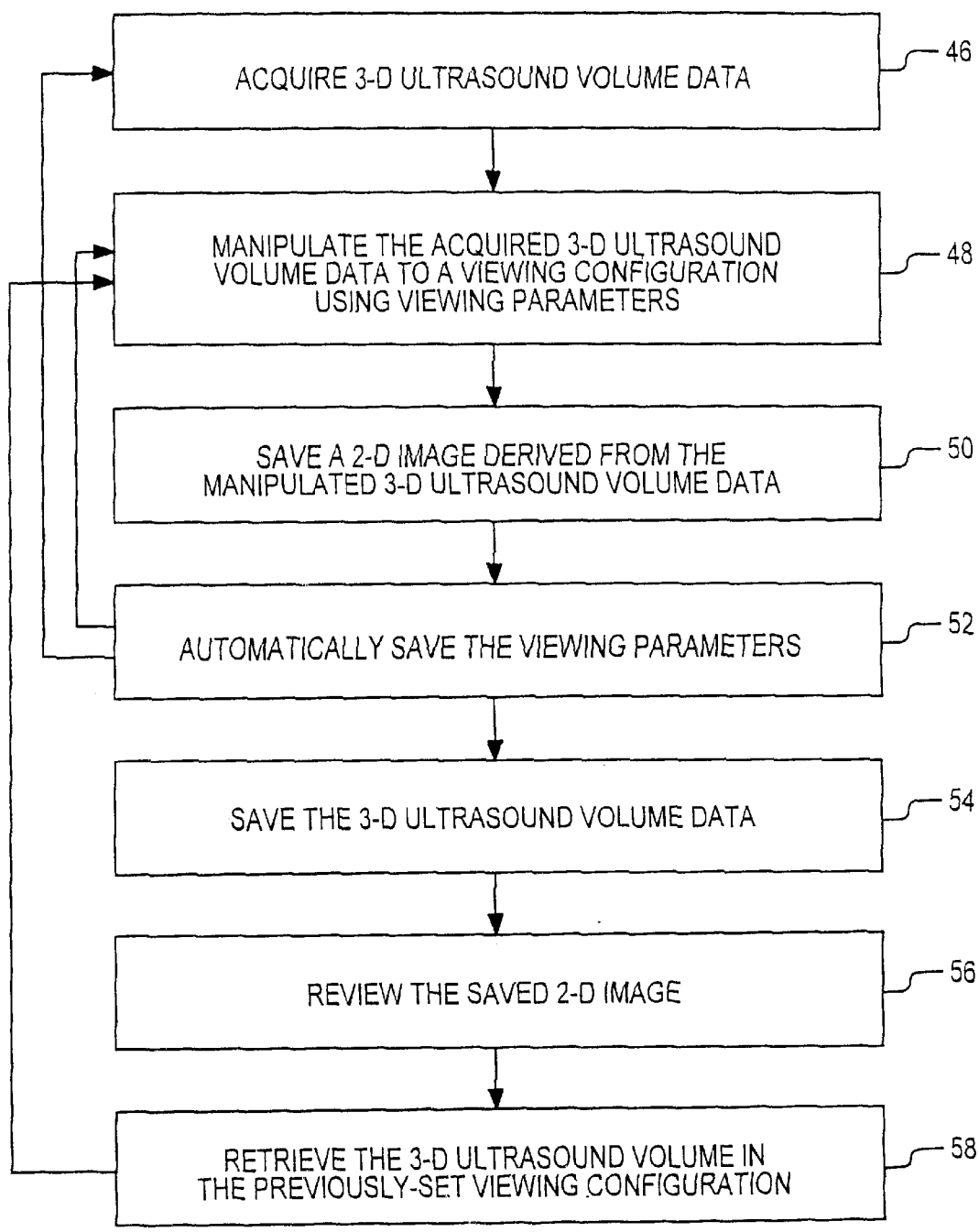
FIG. 4 is a flow diagram of a method of managing 2-D images, including any saved 3-D ultrasound volume data that was used to derive the 2-D images, using the system of FIG. 1 in accordance with the invention.

A method of managing 2-D images, as well as any saved 3-D ultrasound volumes that were used to derive the 2-D images, using the ultrasound imaging system 10 of FIG. 1 will be described with reference to FIG. 4. At step 46, 3-D ultrasound volume data of an anatomical structure is acquired by scanning the ultrasonic scanhead 12 on a patient over an area that coincides with the anatomical structure of interest. In a well known manner, ultrasound waves are transmitted from the scanhead and then echoes of the ultrasound waves that have been reflected from the anatomical structure are received by the scanhead. The received ultrasound echoes are converted into electrical signals and transmitted to the processor 30 of the processing unit 14. Using conventional 3-D imaging software, the processor acquires the 3-D ultrasound volume data of the anatomical structure by processing the received electrical signals. During step 48, the acquired 3-D ultrasound volume data is manipulated to a desired viewing configuration using a number of viewing parameters to capture a 2-D image. As an example, the viewing parameters may include orientation, geometry, rendering algorithm (e.g., surface rendering and arbitrary slicing), colormaps, and ultrasound imaging parameters. The exact types of viewing parameters that are used to manipulate the 3-D ultrasound volume data are not critical to the invention.

During step 50, the 2-D image derived from the manipulated 3-D ultrasound volume data is then manually saved by the user of the ultrasound imaging system 10. As an example, the saving procedure may be initiated when a key is depressed on the input device 16. The 2-D image may be saved in the memory 22 or the removable storage device 26 of the system. At step 52, the bookmark saver 24 of the processing unit 14 automatically saves the viewing parameters in response to the manual saving of the 2-D image. Furthermore, the bookmark saver saves the information that identifies the 3-D ultrasound volume from which the 2-D image was derived. In a preferred embodiment, the 2-D bitmap data of the 2-D image, the viewing parameter settings, and the identification information are collectively saved as a bookmark. Additional 2-D images may then be derived from the acquired 3-D ultrasound volume by changing one or more viewing parameters to manipulate the 3-D ultrasound volume data to different viewing configurations. Furthermore, the steps 46 through 52 may be repeated to acquire additional 3-D ultrasound volumes from the anatomical structure. If repeated, one or more 2-D images may be derived from each additionally acquired 3-D ultrasound volume.

At step 54, at least one acquired 3-D ultrasound volume is saved. Although step 54 is described here and shown in FIG. 3 to follow step 52, step 54 may be executed anytime after step 46 during which the saved 3-D ultrasound volume is acquired by the ultrasound imaging system 10. After all the 3-D ultrasound volume data of interest and the viewing parameters for each desired 2-D image have been saved, one or more saved 2-D images are reviewed by displaying the 2-D images on the display device 18 of the system, during step 56. Assuming that the underlying 3-D ultrasound volume had been previously saved, the 3-D ultrasound volume is retrieved using the saved viewing parameters via the 2-D image being reviewed, during step 58, such that the 3-D volume data is in the same viewing configuration as when the 2-D image was saved. That is, the viewing parameters for the 3-D ultrasound volume data are set exactly as they were set when the 2-D image was saved. Thus, the user of the system does not have to reset the viewing parameters to manipulate the retrieved 3-D ultrasound volume data to the previously set viewing configuration, thereby allowing the user to readily pick up the work of capturing and saving 2-D images. Since this work can easily be continued at any time, the duration of an ultrasound examination can be shortened by performing some or most of the work after the examination, as long as the underlying 3-D ultrasound volumes are saved.

Although the system and the method in accordance with the invention have been described with respect to ultrasound imaging, other embodiments of the invention are possible. For example, the system may be an imaging system based on magnetic resonance, computed tomography technology, or other modalities. Alternatively, the system may be a conventional computer system that embodies the bookmark saver. Consequently, the method can also be modified so that steps of the modified method are executed by a system in accordance with one of these alternative embodiments.

What is claimed is:

1. A method of managing data comprising steps of:
   acquiring a three-dimensional volume for a target structure;
   manipulating said three-dimensional volume to a specific viewing configuration using at least one user-selectable viewing parameter to derive a two-dimensional image of interest from said three-dimensional volume, said specific viewing configuration thereby corresponding to deriving of said two-dimensional image;
   saving said two-dimensional image of interest as an image file, including saving said viewing parameter that was used to derive said two-dimensional image, including forming links of said image file with said saved viewing parameter and with said three-dimensional volume;
   saving said three-dimensional volume in a storage medium;
   reviewing said two-dimensional image subsequent to said saving of said two-dimensional image and said three-dimensional volume, including displaying said link to said three-dimensional volume as an automated response to accessing said image file; and
   retrieving said saved three-dimensional volume in said viewing configuration from said storage medium and re-manipulating said three-dimensional volume into said specific viewing configuration as automated responses to accessing said links.

2. The method of claim 1 wherein said step of saving said viewing parameter includes a step of embedding information regarding said viewing parameter into said image file such that said image file contains information related to said two-dimensional image and said viewing parameter.

3. The method of claim 2 further comprising a step of embedding identifying information into said image file, said identifying information indicating that said three-dimensional volume is the data from which said two-dimensional image was derived.

4. The method of claim 1 wherein said step of manipulating said three-dimensional volume to said specific viewing configuration using at least one user-selectable viewing parameter is a step of selecting a desired setting for at least one imaging parameter.

5. The method of claim 1 wherein said step of reviewing said saved two-dimensional image includes a step of displaying said two-dimensional image with a visual cue which indicates whether said three-dimensional volume associated with said two-dimensional image has been saved.

6. The method of claim 5 wherein said step of displaying said two-dimensional image is a step of displaying said two-dimensional image with a descriptive text that indicates whether said three-dimensional volume has been saved.

7. The method of claim 5 wherein said step of displaying said two-dimensional image is a step of displaying said two-dimensional image with a pictorial graphic element that indicates whether said three-dimensional volume has been saved.

8. A system for managing data comprising:
   image processing means for manipulating acquired three-dimensional volume data of a target structure to a specific viewing configuration using at least one user-selected viewing parameter to capture a two-dimensional image of interest from said three-dimensional volume data, said specific viewing configuration thereby corresponding to said capture of said two-dimensional image;

storage means operatively coupled to said image processing means for storing said three-dimensional volume data and said two-dimensional image as individual files;

display means operatively coupled to said storage means for displaying said three-dimensional volume data and said two-dimensional image; and saving means operatively coupled to said display means and said storage means for automatically saving parameter data relating to said viewing parameter when said two-dimensional image is saved, said saving means and said storage means being configured to establish links among said parameter data and said individual files, such that said parameter data is used to display said three-dimensional volume data in said specific viewing configuration on said display means as an automated response when said three-dimensional volume data is retrieved in cooperation with opening said two-dimensional image.

9. The system of claim 8 wherein said saving means is configured to embed information regarding said viewing parameter with image data of said two-dimensional image in a single data file.

10. The system of claim 9 wherein said saving means is further configured to embed identifying information into said data file when said two-dimensional image is saved, said identifying information indicating that said three-dimensional volume data corresponds to said two-dimensional image.

11. The system of claim 8 wherein said image processing means is configured to manipulate said three-dimensional volume data to said specific viewing configuration using at least one imaging parameter.

12. The system of claim 8 wherein said display means is configured to display said two-dimensional image with a visual cue that indicates whether said three-dimensional volume data that corresponds to said two-dimensional image has been saved.

13. The system of claim 12 wherein said display means is configured to display said two-dimensional image with a textual string as said visual cue.

14. The system of claim 12 wherein said display means is configured to display said two-dimensional image with a pictorial graphic element as said visual cue.

15. A method of managing two-dimensional images and corresponding three-dimensional volume data comprising steps of:

acquiring a three-dimensional volume of a target structure;

manipulating said three-dimensional volume to a specific viewing configuration using a plurality of user-selected viewing parameters to extract a two-dimensional image from said three-dimensional volume;

saving said two-dimensional image as an image file, including saving information regarding said plurality of viewing parameters into said image file;

saving said three-dimensional volume in a storage medium as a second file; and as an automated process that is initiated following an opening of said image file, retrieving said second file of said three-dimensional volume from said storage medium using said embedded information regarding said plurality of viewing parameters of said image file such that said three-dimensional volume is automatically manipulated to be displayed in said specific viewing configuration when retrieved.

16. The method of claim 15 wherein said step of saving said two-dimensional image further includes saving identifying information into said image file, said identifying information indicating that said three-dimensional volume includes volume data from which said two-dimensional image was extracted.

17. The method of claim 15 wherein said step of manipulating said three-dimensional volume to said specific viewing configuration using said plurality of viewing parameters includes a step of setting said viewing parameters using at least one imaging parameter.

18. The method of claim 15 further comprising a step of displaying said saved two-dimensional image with a visual cue that indicates whether said three-dimensional volume that corresponds to said two-dimensional image has been saved.

\* \* \* \* \*